United States Patent [19]

Olsson et al.

[11] 4,067,320
[45] Jan. 10, 1978

[54] ARRANGEMENT FOR DRIFT COMPENSATION IN A GAS ANALYZER

[75] Inventors: Sven-Gunnar Olsson, Sollentuna; Rolf Castor, Hagersten; Gabriel Tchang, Stockholm, all of Sweden

[73] Assignee: Siemens Aktiengesellschaft, Berlin & Munich, Germany

[21] Appl. No.: 682,167

[22] Filed: Apr. 30, 1976

[30] Foreign Application Priority Data

May 6, 1975 Germany .................................. 2520197

[51] Int. Cl.² ............................ A61B 5/00; G01N 31/00
[52] U.S. Cl. ................................... 128/2 C; 73/23; 356/206 X; 250/373
[58] Field of Search .............. 128/2 C, 2 A; 356/204, 356/206; 250/273; 73/23, 23.1

[56] References Cited

U.S. PATENT DOCUMENTS

| 3,308,648 | 3/1967 | Moultou et al. ...................... 73/23 |
| 3,384,746 | 5/1968 | Benz et al. .......................... 250/373 |
| 3,807,876 | 4/1974 | Nakahara et al. ................ 356/206 X |
| 3,826,920 | 7/1974 | Woodroffe et al. ................. 250/373 |
| 3,886,929 | 6/1975 | Hoppesch ........................... 128/2 C |

Primary Examiner—Stephen C. Pellegrino
Attorney, Agent, or Firm—Hill, Gross, Simpson, Van Santen, Steadman, Chiara & Simpson

[57] ABSTRACT

An arrangement for automatic drift compensation in a gas analyzer in which a source of radiation radiates through the gas to be analyzed, and directs the radiation onto a detector. The latter forms an amplified output signal corresponding to the detector output and corresponding to the gas concentration. A signal storage stores the signal corresponding to the output signal of the detector when the gas to be analyzed has a predetermined concentration. A comparator compares the output signal from the detector with the stored signal. The gas analyzer is used for determining the content of a predetermined gas in a mixture of gases exhaled by a patient. A circuit connected between the detector output and the comparator input delivers to the storage a signal during the inspiration phase of the patient.

7 Claims, 2 Drawing Figures

ARRANGEMENT FOR DRIFT COMPENSATION IN A GAS ANALYZER

BACKGROUND OF THE INVENTION

The present invention relates to an arrangement for automatic drift compensation in a gas analyzer. A radiation source radiates through the gas to be analyzed and onto a radiation detector which is connected to a circuit for forming an amplified output signal corresponding to the output of the radiation detector and hence corresponding to the gas concentration. Rapid and accurate gas analyzers are required for medical purposes, e.g., for respirator treatments and lung function analysis.

During respirator treatments, the correct treatment is determined on the basis of the $CO_2$ content of the gas exhaled by the patient. It is, therefore, necessary to determine the $CO_2$ content quickly and accurately. A photometric measuring method is the most expedient method. Here the transfer properties of the gas exhaled by the patient for the rays of a light source are used to determine the $CO_2$ content.

It is already known in the art that by means of a suction pump, gas samples can be taken continuously or intermittently from the gas mixture exhaled by a patient and the samples may be delivered to a special measuring chamber for analysis, to determine the $CO_2$ content, for example. Due to the fact that $CO_2$ is mixed with other gases, and to the delay caused by the hose connection between the respirator and the measuring chamber, there develops a deformation of the recorded $CO_2$ curve. As a result, the phase relation between the $CO_2$ curve and the actual gas flow curve in the respirator hose cannot be accurately established. It is, therefore, more advantageous to use a radiation source of suitable spectral distribution and to direct the radiation coming from the radiation source directly to the gas flowing to or away from the patient. It is preferable to direct it to a detector via a radiation interrupter and a suitable filter.

Due to the low signal levels requiring the use of amplifiers with large gains, and because of interferences stemming from the varying radiation intensity of the radiation source and from dirt deposits on the glass terminating the gas line, problems arise with respect to drift compensation.

It is, therefore, the object of the present invention to provide an arrangement in which automatic drift compensation takes place.

Another object of the present invention is to provide an arrangement of the foregoing character which may be economically fabricated and maintained in service.

A further object of the present invention is to provide an arrangement, as described, which has a substantially long operating life.

SUMMARY OF THE INVENTION

The objects of the present invention are achieved by providing a circuit arrangement with a storage to which a circuit element is connected that brings about the storage of a signal corresponding to the output signal when the gas to be analyzed has a known concentration. The storage is connected to a comparator which compares the output signal furnished by the detector with the signal stored in the storage. In the present invention, the drift-dependent component in the output voltage of the detector, is eliminated by comparing the actual output voltage with the voltage corresponding to a known gas concentration, e.g., during the previous inhalation. Since the drift variations proceed relatively slowly, the null line of the voltage signal corresponding to the gas content will not vary appreciably between the time of storage and the comparison. In a particularly advantageous embodiment of the present invention, the circuit element applies to the storage, during the inspiration phase, a signal corresponding to the output signal. Since with the $CO_2$ measurement, the $CO_2$ content of the inhaled gas is almost zero, and automatic compensation of the zero drift takes place, and the actual output voltage during exhaling accurately indicates the $CO_2$ content.

The novel features which are considered as characteristic for the invention are set forth in paricular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
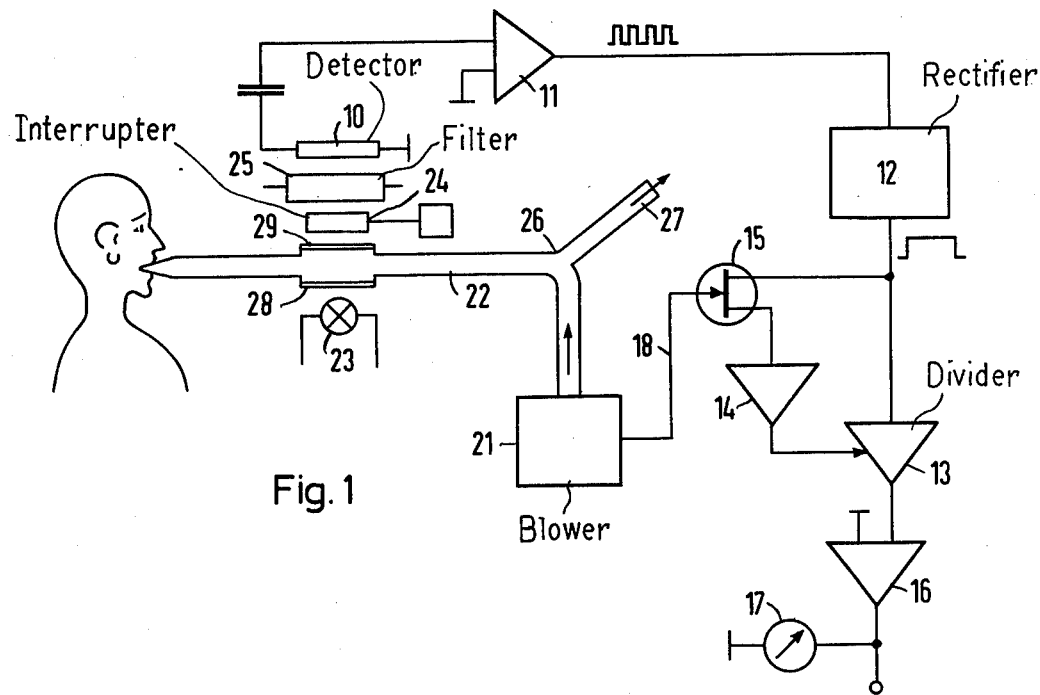
FIG. 1 shows a block diagram of an arrangement in accordance with the present invention.

Referring to the drawing, FIG. 1 shows a hose 22 connecting a patient and a servo blower 21. The servo blower supplies the patient with air during the inspiration phases via the hose branch point 26. The blower may comprise a switching device which periodically releases the air current between a compressed air tank and the patient. An example of such a servo blower is described in U.S. Pat. No. 3,741,208. During the expiration phases, the air exits through the hose end 27. The radiation interrupter 24 is used so that AC amplifiers may be used in the subsequent circuit; these AC amplifiers are more stable than DC amplifiers. The filter 25 passes only those rays which are absorbed by the gas to be measured. The radiation interrupter 24 periodically chops the light rays and is, for example, a light-absorbent flag connected to a mechanical oscillator. FIG. 1 also shows an amplifier 11 which is series connected to a radiation detector 10, a rectifier 12, an electronic divider 13, a storage circuit 14, a field effect transistor 15 associated with storage circuit 14 and divider 13, a linear amplifier 16, and a recording device 17 in the form of a recorder, for example. The output of amplifier 16 may be connected to an additional signal processing device, e.g., to a data acquisition device. The detector 10 is impacted by the radiation of a radiation source 23 which radiates through two windows 28, 29 in hose 22 and through the gas mixture in hose 22.

The radiation delivered to detector 10 is chopped by the radiation interrupter 24 in such a way that the output signal of the detector 10 has a frequency of, e.g., 200 Hz. Before the radiation reaches detector 10, it passes the analysis filter 25 so that only those wavelengths absorbed by the gas to be analyzed are transmitted to detector 10. The output signal of detector 10 obeys the Lambert-Beer Law:

$$U = U_o e^{-xk}$$

where $x$ is the unknown $CO_2$ content; $k$ is an equipment constant not subject to periodic fluctuations; $U$ is the output voltage for a $CO_2$ content of zero. $U_o$ is influenced by the drift (fluctuations of the radiation intensity of radiation source 23, contamination of filter 25, etc.). The pulse-shaped output voltage of detector 10 is amplified in amplifier 11 and then applied to rectifier 12. The output voltage of rectifier 12 represents the mean value of the voltage pulses of amplifier 11 and hence is proportional to the voltage $U_o e^{-xk}$. In order to eliminate the drift in component $U_o$ of the output voltage of rectifier 12, in this embodiment a field effect transistor 15 is located at the output of rectifier 12 and at the storage circuit 14. The field effect transistor 15 becomes conductive when a positive signal appears on its control line 18. From the blower 21, a positive signal is applied to line 18 when the patient inhales, i.e., when the $CO_2$ content is virtually equal to 0. The output voltage obtained by rectifier 12 during this period equals $U_o$, and since the field effect transistor 15 is conductive, this voltage $U_o$ is applied to storage circuit 14. Upon ending the inhaling, the positive signal on line 18 disappears and the transistor 15 blocks storage circuit 14. Now the output signal of rectifier 12 is applied to the one input of divider 13. Simultaneously, the signal of storage 14, which corresponds to $CO_2$ content of zero, is also applied to divider 13. The output signal of divider 13 becomes proportional to the voltage component $e^{-exk}$ because the drift of component $U_o$ is eliminated due to the division in divider 13, and because it is assumed that the drift of $U_o$ between successive inhalation and exhalation phases does not have an effect, which is the case in practice. The output signal of divider 13, which calibrates the zero, is finally delivered to amplifier 16 which has the transfer function 1-log $U_{in}$ (assuming that the relation $U_o e^{-xk}$ holds), so that a signal directly proportional to the desired gas content is obtained at the output of amplifier 16.

This behavior is repeated when the field effect transistor 15 is again made conducting by applying a positive signal to its control electrode or gate, when the $CO_2$ content of the gas mixture in tube 22 equals zero, hence during inhaling.

Figure 2:
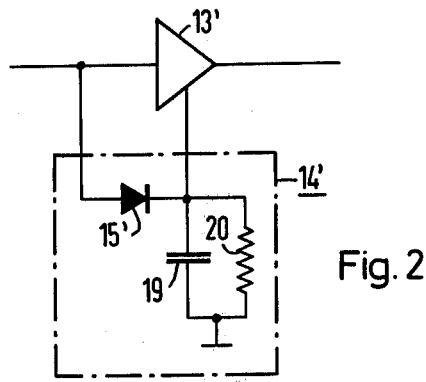
FIG. 2 shows a circuit diagram of an additional embodiment of the present invention.

FIG. 2 shows a schematic of a peak value detector 14' comprising a diode 15', a capacitor 19 and a resistor 20. The resistor 20 can be dispensed with if the leakage resistance of capacitor 19 is sufficient for its discharge during the expiration phases. The divider 13' corresponds to the divider 13 in FIG. 1. The signal of detector 10 is applied to one input of divider 13' and the output of divider 13' is connected to the logarithmic amplifier 16, as in FIG. 1.

During an inhalation phase, the $CO_2$ content of the gas mixture in tube 22 equals approximately zero, and the signal at the input of divider 13' jumps to a maximum value. The diode 15' becomes conducting when the capacitor voltage is lower than or equal to the voltage at the input of circuit 13'. The capacitor is charged during one or several inspiration phases to a voltage which equals the detector voltage associated with inhalation, and hence indicates the $CO_2$ content. This voltage corresponds to the value $U_o$. During exhaling, the signal of detector 10 is delivered to divider 13' since diode 15' is blocked. As described with the embodiment of FIG. 1, a division is performed in divider 13' and the drift-dependent voltage component $U_o$ is eliminated. Hence the output signal formed by the divider 13' is independent of the drift between several successive exhaling phases.

As mentioned before, the leakage resistance of capacitor 19 may be sufficient for its discharge. A resistor 20 may be connected in parallel with capacitor 19. With the embodiment of FIG. 2, a control by blower 21 is not necessary, and hence this embodiment is suitable for arrangements without servo blowers. The idea on which the embodiments of FIGS. 1 and 2 are based, is that the drift of successive inhaling and exhaling phases does not vary appreciably.

The measuring arrangement can also be used when the concentration of actual gas during inhaling is not zero, but is known. Then the compensation is not made for zero, but for the actual value during inhaling.

The present invention is not limited to measuring the $CO_2$ concentration, but can be used generally for measuring gas concentrations. It may be used, for example, for determining the alcohol content in the gas mixture exhaled by a patient.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the means and range of equivalence of the following claims.

We claim:

1. An arrangement for automatic drift compensation in a gas analyzer for detemining the content of a specific gas contained in a gas mixture exhaled by a patient, said arrangement comprising a radiation source for radiating through the gas to be analyzed, a radiation detector onto which the radiation through the gas is directed, circuit means connected to said radiation detector and forming an amplified output signal corresponding to the output of the radiation detector, the output of said radiation detector corresponding to the gas concentration, storage means for storing a signal corresponding to said output signal when the gas to be analyzed has a predetermined concentration, and comparator means connected to said storage means for comparing the output signal from said detector with the signal stored in said storage means, and means connected between the output of the detector and the input of said comparator means for delivering to said storage means the signal corresponding to said output signal during the inspiration phase of a patient.

2. The arrangement as defined in claim 1 including means for supplying air to the patient during the inspiration phase, said means connected between the output of the detector and the input of said comparator means comprising a controllable electronic switch with control input connected to said means for supplying air to the patient.

3. The arrangement as defined in claim 1 with said means connected between the output of the detector and the input of said comparator means being responsive to an output signal having a predetermined value to transmit said signal to said storage means for storage thereby.

4. The arrangement as defined in claim 1 with said storage means comprising capacitor means connected to said means connected between the output of the detector and the input of said comparator means, said means connected between the output of the detector and the input of said comparator means comprising a diode connected for charging said capacitor means during the inspiration phase.

5. The arrangement as defined in claim 1, including chopper means between said radiation source and said detector in periodically interrupting the radiation from said source to said detector; and rectifier means connected between the output of said detector and the input of said comparator means and said storage means, said rectifier means having an output signal proportional to the output voltage of said detector, the output voltage of said detector being pulse-shaped.

6. The arrangement as defined in claim 1, wherein said comparator means comprises divider means.

7. The arrangement as defined in claim 1 including non-linear amplifier means connected to the output of said comparator means and having an output signal directly proportional to the gas concentration to be measured.

* * * * *